United States Patent [19]
Bonne et al.

[11] Patent Number: 4,871,742
[45] Date of Patent: Oct. 3, 1989

[54] PROCESS AND PHARMACEUTICAL COMPOSITIONS FOR THE TREATMENT OF GLAUCOMA

[75] Inventors: Claude Bonne, Montpellier; Claude Coquelet, St Gely Du Fest; Elisabeth Latour, Montpellier, all of France

[73] Assignee: Laboratories Chauvin, Montpellier, France

[21] Appl. No.: 128,579

[22] Filed: Dec. 4, 1987

[30] Foreign Application Priority Data

Dec. 12, 1986 [FR] France ................................. 8617430

[51] Int. Cl.$^4$ ...................... A61K 31/52; A61K 31/50; A61K 31/495
[52] U.S. Cl. ..................................... 514/262; 514/249; 514/913
[58] Field of Search ......................... 514/262, 249, 913

[56] References Cited

U.S. PATENT DOCUMENTS

| | | | |
|---|---|---|---|
| 3,474,098 | 10/1969 | Hitchings et al. | 548/378 |
| 4,425,344 | 1/1984 | Horlington | 514/249 |
| 4,425,345 | 1/1984 | Horlington | 514/249 |
| 4,425,346 | 1/1984 | Horlington | 514/249 |
| 4,478,822 | 10/1984 | Haslam et al. | 514/535 |
| 4,746,675 | 5/1988 | Makino et al. | 514/946 |

FOREIGN PATENT DOCUMENTS

| | | | |
|---|---|---|---|
| 59524 | 9/1982 | European Pat. Off. | 514/249 |
| 22053093 | 1/1974 | France . | |
| 2082455 | 3/1982 | United Kingdom | 514/249 |

OTHER PUBLICATIONS

Chem. Abst. 85:51745j, (1976),–Evans.
Chem. Abst. 103:20745v, (1985),–Mittag et al.
Chemical Abstracts, vol. 68, No. 3, 15-1-68, p. 1100, No. 11642r, Columbus Ohio, U.S.; E. Limmer: "The Effect of Ascorbic Acid or Intraocular Pressure" & Drug Mech. Glaucoma 1966, 153-61, dis. 161-4, * Resume.
Chemical Abstracts, vol. 66, No. 7, 2-13-67, p. 260, No. 27630e, Columbus Ohio, U.S.; M. Virno et al., "Intravenous Glycerol-Vitamin C (Sodium Salt) as Osmotic Agents to Reduce Intraocular Pressure" & Amer. J. Ophthalmol., 62(5), 824–33(1966).

*Primary Examiner*—Douglas W. Robinson
*Assistant Examiner*—Zohreh Fay
*Attorney, Agent, or Firm*—Wegner & Bretschneider

[57] ABSTRACT

The invention relates to a process for the treatment of glaucoma comprising administering to a human in need thereof an effective amount of a compound selected from the inhibitors of xanthine-oxidase.

6 Claims, No Drawings

PROCESS AND PHARMACEUTICAL COMPOSITIONS FOR THE TREATMENT OF GLAUCOMA

The present invention relates to the treatment of glaucoma, and more specifically to pharmaceutical compositions for the treatment of glaucoma.

Primitive open angle glaucoma is an ocular disease leading to the destructions of the optical nerve fibres and to the loss of vision. This destruction is most often accompanied by ocular hypertension; nevertheless, the lesions are not directly co-related to the absolute value of this hypertension.

Present treatments of glaucoma consist in reducing the intra-ocular pressure (IOP), but their efficacy as regards maintaining the visual function has not been proved.

The applicant has observed that the variations of the IOP in animals induces, in a calcium-dependent manner, the appearance of an enzymatic-xanthine-oxidase activity (form 0) at the optical nerve. This enzyme converts hypoxanthine into uric acid without the NAD co-factor, owing to the molecular oxygen. The reaction is accompanied by a production of super-oxide anion ($O_2^-$) and of OH· radical by iron-dependent conversion, causing cellular lesions and the destruction of the neurons.

The present invention aims, therefore, at providing therapeutic compositions able to prevent the lesions induced by this mechanism.

The present invention thus relates to a process for the treatment of glaucoma, comprising administering to a human in need thereof an effective amount of a compound selected from the inhibitors of xanthine-oxidase.

The applicant has discovered further that particularly favourable results could be obtained by using a combination of an inhibitor of xanthine-oxidase and a free oxygenated radical scavenger and possibly of a chelating agent of iron.

The inhibitors of xanthine-oxidase can in particular be allopurinol, oxypurinol, folic acid and the flavonoids such as myricetin and kaempferol.

The free oxygenated radical scavenger can in particular be tocopherol, ascorbic acid, the ubiquinones, the pharmaceutically acceptable salts of dihydroxy-2,5-benzene sulphonic acid (particularly ethamsylate), the peroxydases, the derivatives of caffeic acid and anetholtrithione.

The chelating agents of iron can in particular be deferoxamine, ethylenediamino-N,N'-di(o.hydroxyphenylacetic) acid, 2,2'-bipyridine, nitrolotriacetic acid and pyridoxal isonicotinoylhydrazone.

A particularly preferred composition is that comprising:

(a) the combination of allopurinol and ethamsylate. As examples of other combinations, there can be cited:

(b) the combination of allopurinol and tocopherol and possibly of ascorbic acid.

(c) the combination of folic acid, tocopherol and ascorbic acid.

(d) the combination of keampferol and tocopherol.

(e) the combination of myricetin and ethamsylate.

(f) the combination of allopurinol and anetholtrithione.

The following table gives the usable doses in man for different active principles:

| Compound | dose mg/day |
| --- | --- |
| allopurinol | 100 to 1000 |
| anetholtrithione | 20 to 100 |
| tocopherol | 100 to 1000 |
| ascorbic acid | 300 to 2000 |
| folic acid | 20 to 100 |
| ethamsylate | 300 to 1000 |

The active principles according to the invention can be administered to man or to animals by topical, oral or parenteral route.

These active principles can be put in the form of solid, semi-solid or liquid pharmaceutical compositions. As examples, there can be cited tablets, capsules, suppositories, injectable solutions or suspensions, as well as forms with sustained release.

In these compositions, the active principle is generally mixed with one or more of the usual pharmaceutically acceptable excipients well known to a man skilled in the art.

The therapeutic compositions which can be administered by topical route contain in particular from 0.1 to 5% of active principle.

The therapeutic compositions which can be administered by oral or parenteral route can contain in particular from 1 to 60% by weight of active principle.

The following can be cited as examples of compositions.

| Tablets | |
| --- | --- |
| allopurinol | 200 mg |
| ethamsylate | 200 mg |
| starch | 60 mg |
| Avicel pH10.2 | 90 mg |
| monosodium citrate | 10 mg |
| polyvinylpyrolidone | 20 mg |
| magnesium stearate | 20 mg |
| Capsules | |
| allopurinol | 200 mg |
| ascorbic acid | 200 mg |
| magnesium stearate | 10 mg |
| Drinkable solution | |
| allopurinol | 200 mg |
| double succinate of tocopherol and of PEG | 400 mg |
| sorbitol | 1.5 g |
| ethyl alcohol, 95% | 0.2 ml |
| aromatic composition | q.s. |
| water | q.s. for 10 ml. |

What is claimed is:

1. A process for the treatment of glaucoma comprising administering to a human in need thereof a therapeutically effective amount for the treatment of glaucoma of a compound selected from the group consisting of allopurinol, oxypurinol and the flavonoids.

2. A process as claimed in claim 1, wherein the compound is allopurinol.

3. A process as claimed in claim 2, wherein 100 to 1000 mg/day of allopurinol is administered to a human in need thereof.

4. A process as claimed in claim 2, wherein the allopurinol is administered orally.

5. A process as claimed in claim 2, wherein the allopurinol is administered parenterally.

6. A process as claimed in claim 2, wherein the allopurinol is administered topically.

* * * * *